US011980148B2

(12) United States Patent
Isozaki et al.

(10) Patent No.: US 11,980,148 B2
(45) Date of Patent: May 14, 2024

(54) NEUTRON RAY IRRADIATION TARGET APPARATUS, MUTATION INDUCTION METHOD, AND IRRADIATION TARGET MANUFACTURING METHOD

(71) Applicant: Quantum Flowers & Foods Co., Ltd., Mito (JP)

(72) Inventors: Hiroya Isozaki, Mito (JP); Norio Kikuchi, Mito (JP); Kohei Yamaguchi, Mito (JP)

(73) Assignee: Quantum Flowers & Foods Co., Ltd., Mito (JP)

( * ) Notice: Subject to any disclaimer, the term of this patent is extended or adjusted under 35 U.S.C. 154(b) by 0 days.

(21) Appl. No.: 17/927,738

(22) PCT Filed: Jun. 20, 2022

(86) PCT No.: PCT/JP2022/024585
§ 371 (c)(1),
(2) Date: Nov. 25, 2022

(87) PCT Pub. No.: WO2023/007986
PCT Pub. Date: Feb. 2, 2023

(65) Prior Publication Data
US 2023/0210072 A1    Jul. 6, 2023

(30) Foreign Application Priority Data

Jul. 29, 2021   (JP) .................................. 2021-124258
Nov. 9, 2021    (JP) .................................. 2021-182268

(51) Int. Cl.
*A01H 1/06*   (2006.01)
*C12M 1/42*   (2006.01)
*C12N 15/01*  (2006.01)
*G21K 5/08*   (2006.01)

(52) U.S. Cl.
CPC .............. *A01H 1/06* (2013.01); *C12M 35/00* (2013.01); *C12N 15/01* (2013.01); *G21K 5/08* (2013.01)

(58) Field of Classification Search
CPC .......... G21K 5/08; A01H 1/06; C12M 35/00; C12N 15/01
See application file for complete search history.

(56) References Cited

U.S. PATENT DOCUMENTS

| 4,029,967 | A | | 6/1977 | Tetzlaff | |
| 5,107,524 | A | * | 4/1992 | Yamaguchi | ......... G03F 7/70733 378/69 |
| 2008/0273661 | A1 | * | 11/2008 | Kirk | .................. G21K 5/10 378/69 |
| 2011/0119786 | A1 | | 5/2011 | Thompson et al. | |
| 2013/0160161 | A1 | | 6/2013 | Bart et al. | |
| 2017/0118829 | A1 | | 4/2017 | Hartman et al. | |
| 2017/0225816 | A1 | | 8/2017 | Sasaki et al. | |
| 2021/0025796 | A1 | | 1/2021 | Czerniawski et al. | |

FOREIGN PATENT DOCUMENTS

| CN | 107422363 A | 12/2017 |
| CN | 112841026 A | 5/2021 |
| EP | 2612692 A | 7/2013 |
| JP | H03-48200 A | 3/1991 |
| JP | H08-179100 A | 7/1996 |
| JP | H10-127195 A | 5/1998 |
| JP | 2001-42047 A | 2/2001 |
| JP | 2004-347510 A | 12/2004 |
| JP | 2012-50698 A | 3/2012 |
| JP | 2013-176396 A | 9/2013 |
| JP | 2017-90200 A | 5/2017 |
| JP | 2019-83740 A | 6/2019 |
| WO | 2009/119914 A | 10/2009 |
| WO | 2016/059990 A | 4/2016 |

OTHER PUBLICATIONS

Lochlainn, S. et al. New Phytologist (2011) 189: 409-414. (Year: 2011).*
International Search Report for PCT/JP2022/024585 dated Aug. 16, 2022.
PCT written opinion dated Aug. 16, 2022.
Japanese Notice of reasons for refusal dated Sep. 8, 2021 for application No. JP2021-124258.
Japanese Notice of reasons for refusal dated Dec. 14, 2021 for application No. JP2021-182268.
Richard H. Howard, et al., "Mechanical performance of neutron-irradiated dissimilar transition joints of aluminum alloy 6061-T6 and 304L stainless steel", Journal of Nuclear Materials, pp. 348-353, 2018.
English translation of International Search Report for PCT/JP2022/024585 dated Feb. 2, 2023.

* cited by examiner

*Primary Examiner* — Russell Kallis
(74) *Attorney, Agent, or Firm* — Yokoi & Co., U.S.A.; Toshiyuki Yokoi

(57) ABSTRACT

A neutron ray irradiation target apparatus 100 of the present invention is used to irradiate irradiation targets (seeds, etc.) with a neutron ray generated by a neutron ray irradiation apparatus. The neutron ray irradiation target apparatus 100 has a holding means 70 for holding the irradiation targets. The holding means 70 holds at least one closed container 30 which can accommodate the irradiation targets 20 stacked randomly and three-dimensionally. In the case where the irradiation targets are stacked three-dimensionally and accommodated in the closed container, the irradiation targets overlapping each other are irradiated with the neutron ray in a chain reaction fashion. The neutron ray irradiation target apparatus 100 can be used in a method for irradiating a large amount of irradiation targets (seeds of crops, etc.) with a neutron ray, while reducing a required time, thereby efficiently inducing mutations in the irradiation targets.

8 Claims, 11 Drawing Sheets

FIG. 5

|  | NUMBER OF NEUTRONS (n/s/cm$^2$) | ENERGY |
|---|---|---|
| METHOD A | $4.8 \times 10^7$ | <0.4(eV) |
| METHOD B | $1.2 \times 10^7$ | >1(MeV) |
| METHOD C | $1.2 \times 10^6$ | >10(MeV) |

FIG. 6

| ITEM / IRRADIATION TIME | NUMBER OF SOWED SEEDS | NUMBER OF PISTIL ANOMALIES | PISTIL ANOMALY RATIO [%] | NUMBER OF NON-BOLTING PLANTS | NON-BOLTING PLANT RATIO [%] | PETAL ANOMALY (SPOT) | PETAL ANOMALY (SPOT) [%] |
|---|---|---|---|---|---|---|---|
| CTRL (0 MINUTE) | 257 | 12 | 5 | 12 | 5 | 0 | 0 |
| 5 MINUTE IRRADIATION | 206 | 32 | 16 | 21 | 10 | 20 | 10 |
| 10 MINUTE IRRADIATION | 236 | 13 | 6 | 15 | 6 | 13 | 6 |
| 1 HOUR IRRADIATION | 225 | 43 | 19 | 8 | 4 | 40 | 18 |
| 2 HOUR IRRADIATION | 248 | 88 (※) | 36 | 41 | 17 | 88 (NO PETAL) | 36 (NO PETAL) |

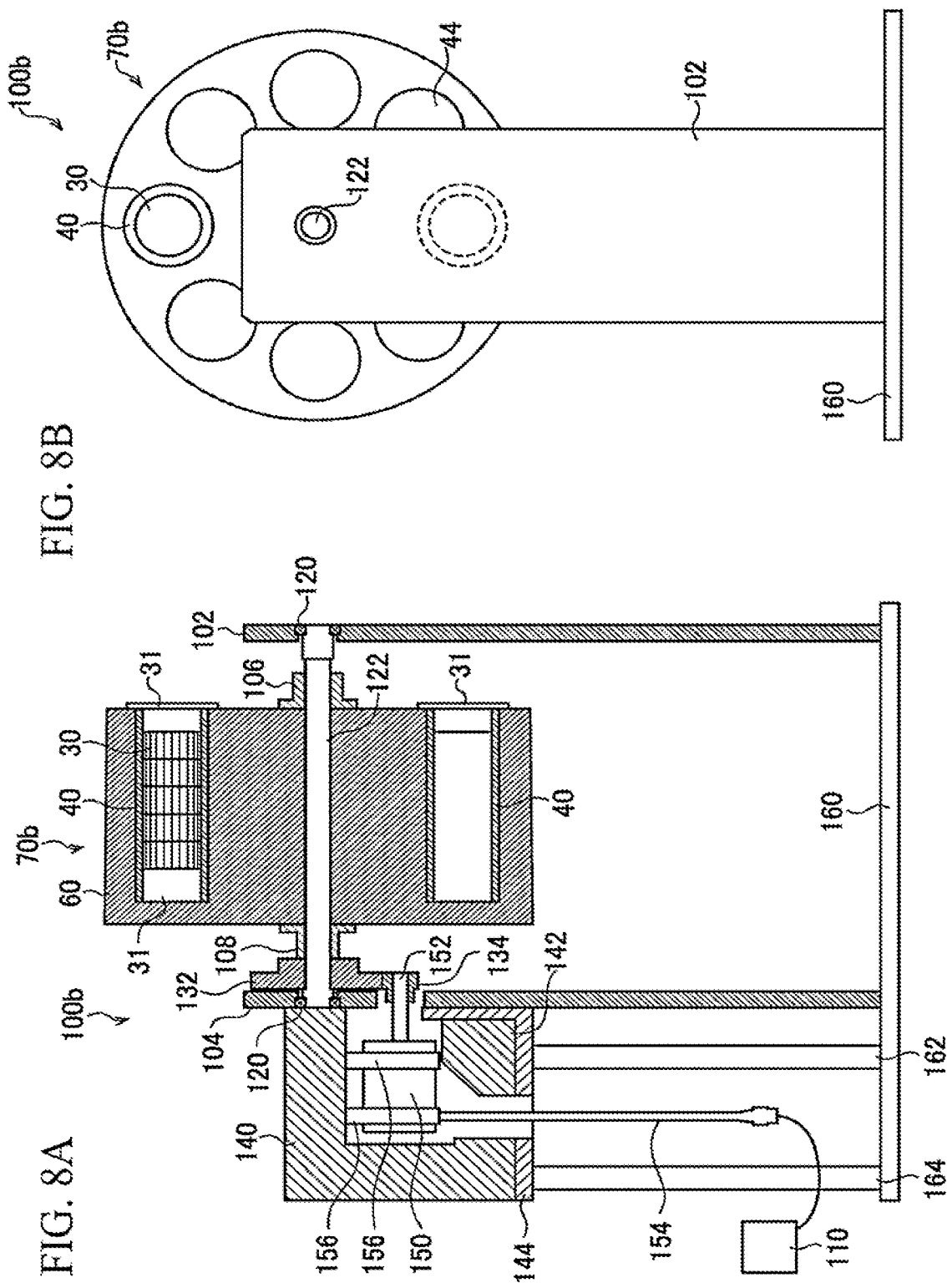

NEUTRON RAY IRRADIATION TARGET APPARATUS, MUTATION INDUCTION METHOD, AND IRRADIATION TARGET MANUFACTURING METHOD

TECHNICAL FIELD

The present invention relates to a neutron ray irradiation target apparatus which is used when plant seeds or the like are irradiated with a neutron ray from a neutron ray irradiation apparatus and in which the plant seeds or the like are accommodated, to a mutation induction method for inducing mutation in the seeds or the like using the neutron ray irradiation target apparatus, and to a method for producing an irradiation target.

BACKGROUND ART

Conventional methods for inducing mutation in plants related to agricultural crops or forestry crops include a chemical agent treatment and a radioactive ray irradiation treatment. The chemical agent treatment employs a chemical mutation induction substance having a mutagenicity, such as an alkylating agent, as in an ethyl methanesulfonate (EMS) treatment. In the case of ethyl methanesulfonate (EMS) treatment, only a point mutation of mainly G:C→A:T is obtained, and it is difficult to attain knockout of a plurality of genes duplicated in tandem, modification of a promotor region, or the like. Also, ethyl methanesulfonate (EMS) is highly toxic. Therefore, when seeds are treated excessively, the seeds may fail to germinate or may be damaged.

Meanwhile, in the radioactive ray irradiation treatment which does not use any chemical agent, a radioactive ray, such as gamma-ray, X-ray, heavy ion beam, or neutron ray, is applied to a seed of a plant or the embryo thereof, or the entirety or a part of the plant, thereby inducing mutation. Among the above-described radioactive rays, X-ray and gamma-ray are high in substance penetrability and can be applied externally.

A treatment using X-ray or gamma-ray induces mutation in DNA (deoxyribonucleic acid) through ionizing action. The treatment by X-ray or gamma-ray, which are low LET (linear energy transfer) rays, has an advantage in that it can be applied to a large amount of irradiation targets such as seeds. However, in the case of using a low LET ray, which sporadically applies energy in a wide range, DNA damage occurs sporadically, and the width (spectrum) of mutation becomes narrow. Therefore, this treatment can increase the mutagenesis rate only to about 10 to 100 times the natural mutagenesis rate, which is about one hundred-thousandth to one millionth. Accordingly, in order to obtain a desired amount of mutants, a large amount of irradiated samples are needed, along with a large breeding space, massive manpower, and a long period of time.

Of the radioactive rays, a heavy ion beam is a high LET ray which causes its ionizing action locally. Therefore, as compared with the case where X-ray or gamma-ray is used, the width (spectrum) of mutation is wider, and a resultant mutant has a smaller number of accompanying mutations. Also, the required dose is low and the irradiation effect is high. However, its substance penetrability is low, so that its penetration distance is very short (several tens of μm (micrometers) from the surface of a substance). Therefore, it is not possible to irradiate many seeds, and a long time is still needed to obtain a desired amount of mutants.

Of radioactive rays, a neutron ray is a high LET ray, which is high in biological effect like a heavy ion beam. Use of neutron ray results in a high mutagenesis rate and a high irradiation effect. Therefore, use of neutron ray is considered as a potent method for effectively obtaining mutants. Patent Documents 1 and 2 disclose examples of a conventional technique which uses neutron ray, and Patent Document 3 discloses a neutron ray generation apparatus.

For example, Patent Document 1 discloses a technique of applying a radioactive ray to a flowering plant having a particular genotype, thereby creating a mutant of the flowering plant. In this publication, ion beam, X-ray, gamma-ray, electron beam, neutron ray, etc. are mentioned as example types of radioactive rays. However, only ion beam is disclosed in the embodiment.

Also, Patent Document 2 describes that a physical mutagen, such as an energy beam, including X-ray, gamma-ray, neutron ray, particle beam, heavy ion beam, etc., is used to produce a Euglena with reduced motility. However, in this publication as well, irradiation of heavy ion beam is disclosed as a concreate example. Notably, Patent Document 4 discloses a technique of irradiating the embryos of barley seeds with a beam of ions transported from an accelerator, while controlling the depth of irradiation, by using a depth control irradiation apparatus. Also, utilization of neutron ray for anomaly diagnosis is described in Patent Document 5.

PRIOR ART DOCUMENTS

Patent Documents

Patent Document 1: WO2009/119914
Patent Document 2: Japanese Patent Application Laid-Open (kokai) No. 2019-83740
Patent Document 3: Japanese Patent Application Laid-Open (kokai) No. 2012-50698
Patent Document 4: Japanese Patent Application Laid-Open (kokai) No. H10-127195
Patent Document 5: Japanese Patent Application Laid-Open (kokai) No. 2017-90200

Non-Patent Document

Non-patent Document 1: "J-PARC", [online], Japan Proton Accelerator Research Complex, [searched on Jun. 2, 2021], Internet, <URL:https://j-parc.jp/c/index.html>

SUMMARY OF THE INVENTION

Problem to be Solved by the Invention

As described above, of radioactive rays which induce mutation, X-ray and gamma-ray are high in substance penetrability and can be applied to a large amount of irradiation targets such as seeds. However, X-ray and gamma-ray have a drawback in that the width of mutation is narrow, and their mutation induction rates are low. Also, as described in Patent Document 4, when a heavy ion beam is used, the width of mutation becomes wider as compared with the case of using X-ray or gamma-ray. However, its substance penetrability is low and its penetration distance is several tens of μm (micrometers) from the surface of a substance. In the case where a heavy particle beam is applied to irradiation targets, the irradiation targets must be disposed on an irradiation surface such that they do not overlap each other. Therefore, in the case where a heavy particle beam is applied to a large amount of irradiation targets, a lot of time and labor is needed to dispose them onto the irradiation surface. In addition, a complex apparatus such as a depth control irradiation apparatus and a transportation apparatus or the like for transporting irradiation targets within an irradiation path are needed.

In contrast to these, neutron ray is a high LET ray having a high biological effect like a heavy ion beam, and use of a high neutron ray results in a high mutagenesis rate and a high irradiation effect. Therefore, use of neutron ray is considered as a potent method for effectively obtaining mutants. However, a neutron ray generation apparatus is very, very expensive. Therefore, the neutron ray generation apparatus might be used in the case where there is financial leeway, such as the case of an intractable disease curing apparatus or in the case where no alternative exists, but the frequency of its use is low.

In general, a large neutron ray generation apparatus is shared in many cases like the above-described "J-PARC." Moreover, the neutron ray generation apparatus is not operated at all times, and is operated in limited periods. Therefore, in general, times of use allotted to an individual user and to an individual test are limited.

In reality, it is almost impossible to employ neutron ray irradiation for plant breeding under such an environment, and therefore, not much consideration has been given to its use. Namely, although induction of mutation by neutron ray irradiation can be performed theoretically as described in the above-described Patent Documents 1 and 2 by using the apparatus described in the above-described Patent Document 3, such mutation induction is not considered a viable approach, and there have been no specifically feasible methods available.

In view of the above, an object of the present invention is to provide a neutron ray irradiation target apparatus which enables application of a neutron ray to a large amount of irradiation targets such as crop seeds or the like (in particular those which are small in size), while reducing the required time, by using a neutron ray irradiation apparatus.

Means for Solving the Problem

The present invention, which achieves the above-described object, has the following features.

[1] A neutron ray irradiation target apparatus which is used for irradiating irradiation targets with a neutron ray generated by a neutron ray irradiation apparatus. Each of the above-described irradiation targets is at least one member selected from a group consisting of a seed of a plant, an embryo of a plant, the entirety or part of a plant, yeast, and microorganisms. The above-described neutron ray irradiation target apparatus comprises holding means for holding the above-described irradiation targets. The above-described neutron ray irradiation target apparatus is characterized in that the above-described holding means holds at least one closed container which can accommodate the above-described irradiation targets stacked randomly and three-dimensionally therein, the above-described irradiation targets three-dimensionally stacked and accommodated in the above-described closed container are irradiated with the neutron ray, and the above-described neutron ray contains fast neutrons whose energy is greater than 0.1 to 1 MeV, and its irradiation dose is 110 Gy or less.

[2] The neutron ray irradiation target apparatus described in [1], wherein the above-described holding means comprises a plurality of tubular members each of which is opened at at least one end in an axial direction, and a pair of plate members which fixedly support opposite ends of the tubular members in the axial direction, wherein at least one of the above-described closed containers is fixedly held in at least one of the above-described plurality of tubular members.

[3] The neutron ray irradiation target apparatus described in [2], wherein the above-described holding means has a plurality of slots each of which is opened at at least one end in the axial direction, and the above-described tubular members can be attached to the above-described slots.

[4] The neutron ray irradiation target apparatus described in any one of [1] to [3], wherein a center shaft is disposed in a central portion of the above-described holding means, and the neutron ray irradiation target apparatus comprises rotational drive means for rotatively driving the center shaft and control means for controlling the rotational drive means.

[5] The neutron ray irradiation target apparatus described in [4], wherein the above-described closed containers are held on the above-described holding means at a plurality of positions, and the above-described control means intermittently drives the above-described rotational drive means in accordance with an irradiation pattern determined beforehand, thereby changing the above-described closed containers which are to be irradiated with the neutron ray.

[6] The neutron ray irradiation target apparatus described in any one of [1] to [5], wherein each of the above-described irradiation targets held in the above-described closed container is a seed or embryo of a plant.

[7] The neutron ray irradiation target apparatus described in any one of [1] to [5], wherein each of the above-described irradiation targets held in the above-described closed container is the entirety or part of a plant.

[8] The neutron ray irradiation target apparatus described in [6] or [7], wherein the neutron ray emitted from the above-described neutron ray irradiation apparatus contains high energy neutrons.

[9] A mutation induction method for irradiating irradiation targets, held in a closed container of a neutron ray irradiation target apparatus, with neutrons generated by a neutron ray irradiation apparatus, so as to damage DNAs of the above-described irradiation targets, thereby inducing mutations. Each of the above-described irradiation targets is at least one member selected from a group consisting of a seed of a plant, an embryo of a plant, the entirety or part of a plant, yeast, and microorganisms. The mutation induction method is characterized by comprising the steps of holding in the above-described neutron ray irradiation target apparatus the above-described closed container which accommodates the above-described irradiation targets stacked randomly and three-dimensionally; irradiating the above-described irradiation targets with a neutron ray from the above-described neutron ray irradiation apparatus, the neutron ray containing fast neutrons whose energy is greater than 0.1 to 1 MeV, wherein its irradiation dose is 110 Gy or less; cooling the above-described irradiation targets radioactivated as a result of irradiation with the neutron ray; and taking out the above-described irradiation targets from the above-described neutron ray irradiation target apparatus.

[10] A method for manufacturing irradiation targets accommodated in a closed container and mutated, each of the above-described irradiation targets being at least one which is selected from a group consisting of a seed of a plant, an embryo of a plant, the entirety or part of a plant, yeast, and microorganisms and in which a mutation has been induced, the above-described closed container accommodating the above-described mutated irradiation targets stacked randomly and three-dimensionally. The method is characterized by comprising inducing mutations in the above-described irradiation targets by the mutation induction method described in [9], thereby obtaining the mutated irradiation targets accommodated in the above-described closed container.

Effects of the Invention

The present invention enables three-dimensional and random charging of irradiation targets in a plurality of tubular members (slots) provided in the neutron ray irradiation target apparatus. Therefore, the neutron ray, which is a high LET ray, generates secondary radiation rays (alpha-ray, proton-ray, gamma-ray), thanks to its high substance penetrability and nucleus reactions within the irradiation targets (seeds, etc.), thereby cutting DNA by ionization. As a result, neutrons act, in a domino toppling fashion, not only on irradiation targets which are located at positions where they are directly exposed to the neutron ray emitted from the neutron irradiation apparatus, but also on irradiation targets which are located adjacent to the irradiation targets directly exposed to the neutron ray and irradiation targets which are in contact with these irradiation targets, whereby their DNAs can be modified. Namely, the number of mutated irradiation targets among a large amount of the irradiation targets charged in a container densely or three-dimensionally and randomly can be increased remarkably. Also, according to the present invention, the radiation dose of the neutron ray is controlled to a proper value. Therefore, it is possible to avoid damage by neutron irradiation in portions, other than portions where DNA mutations are desired, such as portions relating to occurrence of physiological anomalies such as failure to bud. Thus, the number of individuals in which mutations are induced can be increased to a level which is incomparable with those achieved by known conventional methods.

Also, other modes of the present invention are as follows.

[1] A neutron ray irradiation target apparatus for irradiating irradiation targets with a neutron ray generated by a neutron ray irradiation apparatus, the neutron ray irradiation target apparatus comprising holding means which has a center shaft and which can hold closed containers, each accommodating irradiation targets, in such a manner that the closed containers are located at at least two different locations on a circle whose center is located at the above-described center shaft; rotational drive means for rotatively driving the above-described center shaft; and control means for controlling the above-described rotational drive means.

The above-described neutron ray irradiation target apparatus enables effective irradiation of irradiation targets with a neutron ray within a limited available time. In particular, the neutron ray irradiation target apparatus exhibits an excellent effect when a neutron ray is applied to a large number of small irradiation targets such as seeds. In general, it is difficult to exchange irradiation targets and prepare different irradiation targets during irradiation with the neutron ray. However, in the above-described neutron ray irradiation apparatus, under the control by the control means, the holding means which can hold (is capable of holding) the closed containers rotates so as to move (namely, exchange) the closed containers held at at least two different positions. Therefore, an operator can treat a large number of irradiation targets simultaneously without entering an irradiation zone.

[2] The neutron ray irradiation target apparatus described in [1], wherein the above-described positions include at least a position where the irradiation targets are irradiated with the above-described neutron ray.

[3] The neutron ray irradiation target apparatus described in [2], wherein the above-described control means intermittently drives the above-described rotational drive means in accordance with an irradiation pattern determined beforehand, thereby changing the above-described closed container held at the above-described irradiation position.

The above-described neutron ray irradiation target apparatus makes it possible to change, in accordance with an irradiation pattern determined beforehand, the closed container (irradiation targets) to be irradiated with the neutron ray by control of the control means. The operator can treat a larger number of irradiation targets simultaneously without entering an irradiation zone.

[4] The neutron ray irradiation target apparatus described in any of [1] to [3], wherein the above-described holding means includes a plurality of tubular members each of which is open at at least one end in the axial direction, and a pair of plate-shaped members which fixedly support opposite ends of the tubular members in the axial direction.

[5] The neutron ray irradiation target apparatus described in [4], wherein at least one type of member selected from the group consisting of the above-described tubular members, the above-described plate-shaped members, and the above-described center shaft is formed of at least one type of material selected from the group consisting of aluminum, aluminum alloy, vanadium alloy, ferritic steel, silicon carbide composite material, oxide dispersion strengthened ferritic steel, and boron material.

Even when the above-described material is irradiated with a neutron ray, the half decay period of the above-described material having been radioactivated is short. Therefore, the radiation dose decreases quickly to a background level or less, thereby allowing the material to be carried out from a control region. Accordingly, the neutron ray irradiation target apparatus can be easily carried out after use for a long period of time. Although at least one type of member selected from the group consisting of the above-described tubular members, the above-described plate-shaped members, and the above-described center shaft is preferably formed of the above-described material, it is more preferred that all the members be formed of the above-described material.

[6] The neutron ray irradiation target apparatus described in [5], wherein at least one type of member selected from the group consisting of the above-described tubular members, the above-described plate-shaped members, and the above-described center shaft is formed of an aluminum alloy, and the above-described aluminum alloy contains manganese-55 (Mn55).

When manganese-55 (Mn55) is irradiated with thermal neutrons, gamma-rays are released as a result of the capture reaction, whereby manganese-56 which is a radioactive isotope and whose half-life is 2.6 hours is generated. Accordingly, an effect that the irradiation targets 20 are irradiated secondarily with gamma-rays is also expected.

[7] The neutron ray irradiation target apparatus described in any of [1] to [6] further comprises a shielding member, and the above-described rotational drive means is covered by the above-described shielding member.

Since the rotational drive means is covered by the shielding member, damage of a motor by neutron ray irradiation can be better suppressed.

BRIEF DESCRIPTION OF THE DRAWINGS

FIG. 5 is a table showing the neutron intensity of 1 MW-class neutron flux at a sample position.

FIG. 6 is a table showing the relationship between neutron ray irradiation time and induced mutation for the case of seeds of komatsuna.

FIG. 8A is a perspective view and FIG. 8B is a front sectional view of another embodiment of the neutron ray irradiation target apparatus according to the present invention.

MODES FOR CARRYING OUT THE INVENTION

Figure 1A:
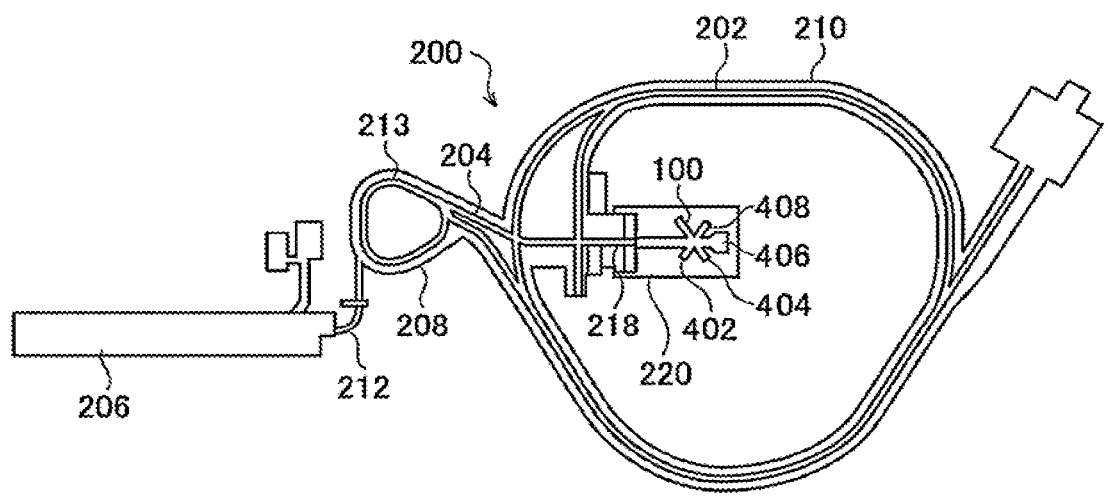
FIG. 1A is a schematic plan view and FIG. 1B is a schematic diagram of a neutron ray irradiation apparatus according to the present invention.
Figure 1B:
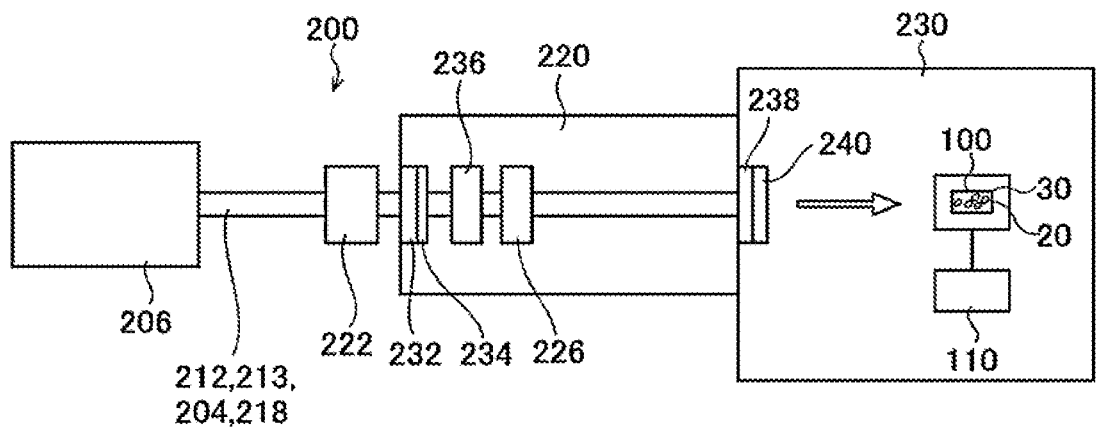

One embodiment of a neutron ray irradiation target apparatus 100 according to the present invention will now be described with reference to the drawings. FIGS. 1A and 1B show a schematic layout drawing (FIG. 1A) of an accelerator 200 in which the neutron ray irradiation target apparatus 100 according to the present invention is disposed, and its schematic configuration (FIG. 1B). The accelerator 200 shown in FIG. 1A has a basic structure which is the same as, for example, that described in Patent Document 5, and is, for example, an accelerator owned by Japan Proton Accelerator Research Complex (J-PARC) described in Non-patent Document 1. Non-patent Document 1 shows that the accelerator 200 of J-PARC consists of three accelerators and three experimental facilities. The accelerators consist of a normal conducting/superconducting linear accelerator (Linac) whose overall length is about 330 m, a 3 GeV proton synchrotron (Rapid Cycling Synchrotron: RCS) whose circumferential length is 348.333 m, and a 50 GeV proton synchrotron (Main Ring: MR) whose circumferential length is 1,567.5 m). Although the accelerator 200 can be used in allotted periods, a time usable for performing a test or experiment one time is limited, and the test or experiment must be performed efficiently.

Various types of particle beams from the accelerator 200 are accelerated within pipe passages 212, 213, and 202 formed in a vacuum container and its branch pipe passages (takeout pipe passages) 204 and 218 by unillustrated superconducting magnets or the like disposed around the pipe passages at intervals in the axial direction, whereby a beam line is formed. A plurality of neutron ray irradiation target apparatuses 100, 402, 404, 406, and 408 are disposed at end portions of the branch pipe passage 218. Since the pipe passages 202, 204, etc. are evacuated to vacuum at the time of neutron ray irradiation, they have an air-tight structure. Since the neutron ray irradiation target apparatuses 100, 402, 404, 406, and 408 are also in a vacuum environment at the time of neutron ray irradiation, these apparatuses must have airtightness so as to prevent erroneous operations in the vacuum environment.

In the embodiment described below, a linear accelerator located on the left end side of the drawing and referred to as a linac 206 is used to generate a neutron ray N. The particle beam generated by the linac 206 and accelerated travels through a small synchrotron (RCS) 208, branches off at the pipe passage 204, which is a takeout beam line, and is guided to the neutron ray irradiation target apparatus 100 disposed in a material/life science experimental facility (MLF) 220. As will be described below, a target (not shown) for generating neutron is disposed on the pipe passage 204 (takeout beam line) side with respect to the neutron ray irradiation target apparatus 100.

FIG. 1B shows a schematic diagram (block diagram) of the accelerator 200 which includes the neutron ray irradiation target apparatus 100 used in the present embodiment. The linac 206, which is an accelerating apparatus of the accelerator 200, accelerates charged particles, thereby emitting a charged particle beam P. The linac 206 is a linear accelerator, and accelerates charged particles (proton, electron, or baryon (in the present example, negative hydrogen ion)), thereby producing a charged particle beam (proton beam, electron beam, or baryon beam) P.

As described above, the accelerated charged particle beam P supplied from the linac 206, which is an accelerating apparatus, is applied in the form of pulses to the material/life science experimental facility 220 at a variable timing via the pipe passage 213, which forms the synchrotron 208, which is a small accelerator. Notably, in the case where further acceleration is needed, the charged particle beam P is guided to the material/life science experimental facility 220 via the pipe passage 202, which forms the synchrotron 210, which is a large accelerator.

In the material/life science experimental facility 220, in order to generate a neutron ray N from the charged particle beam P, the charged particle beam P is first guided to a target 222 within a tank disposed in the material/life science experimental facility 220. In general, carbon and mercury, tantalum, tungsten, or the like which are large in mass number can be used as the material of the target. In the present embodiment, mercury is used as the material of the target. When the charged particle beam P is applied to the mercury target 222, a neutron ray N is generated. The generated neutron ray N is guided to a collimator 226 after passing through a slit 232, a chopper 234, and a filter 236. Thus, the neutron ray N passes through an unillustrated thermal neutron blocker or the like, thereby being adjusted to become a collimated beam. The collimated neutron ray N passes through a collimator 238 and a slit 240, which are provided in an experiment building 230, and is applied to irradiation targets 20 within a closed container 30 fixedly held within the neutron ray irradiation target apparatus 100 in a state in which the beam position is adjusted.

Figure 2B:
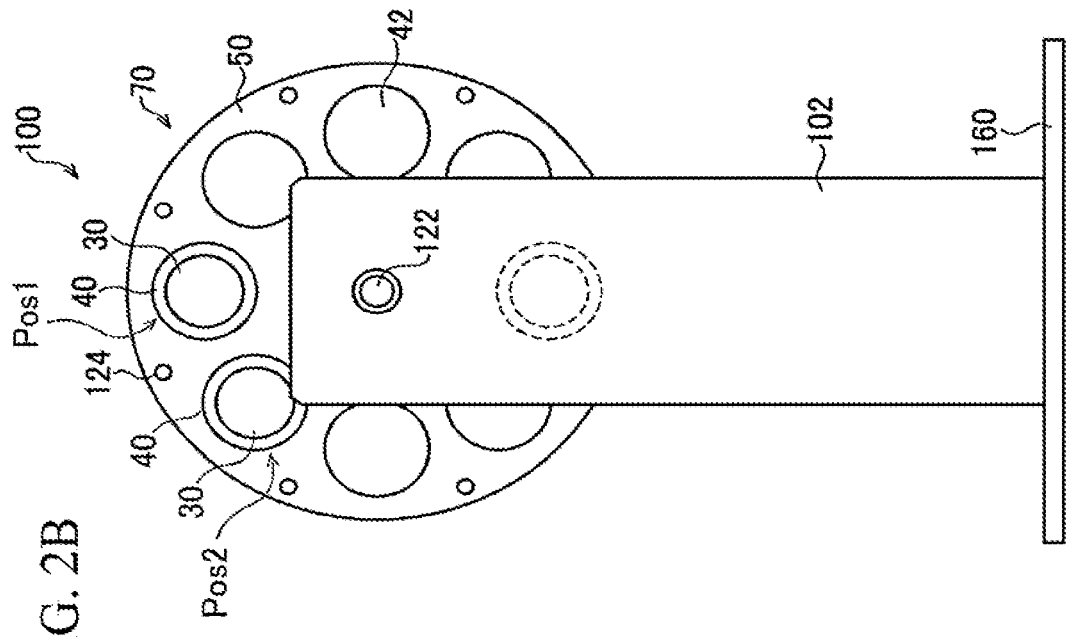
FIG. 2A is a front sectional view and FIG. 2B is a right side view of one embodiment of a neutron ray irradiation target apparatus disposed in the neutron ray irradiation apparatus shown in FIGS. 1A and 1B.
Figure 2A:
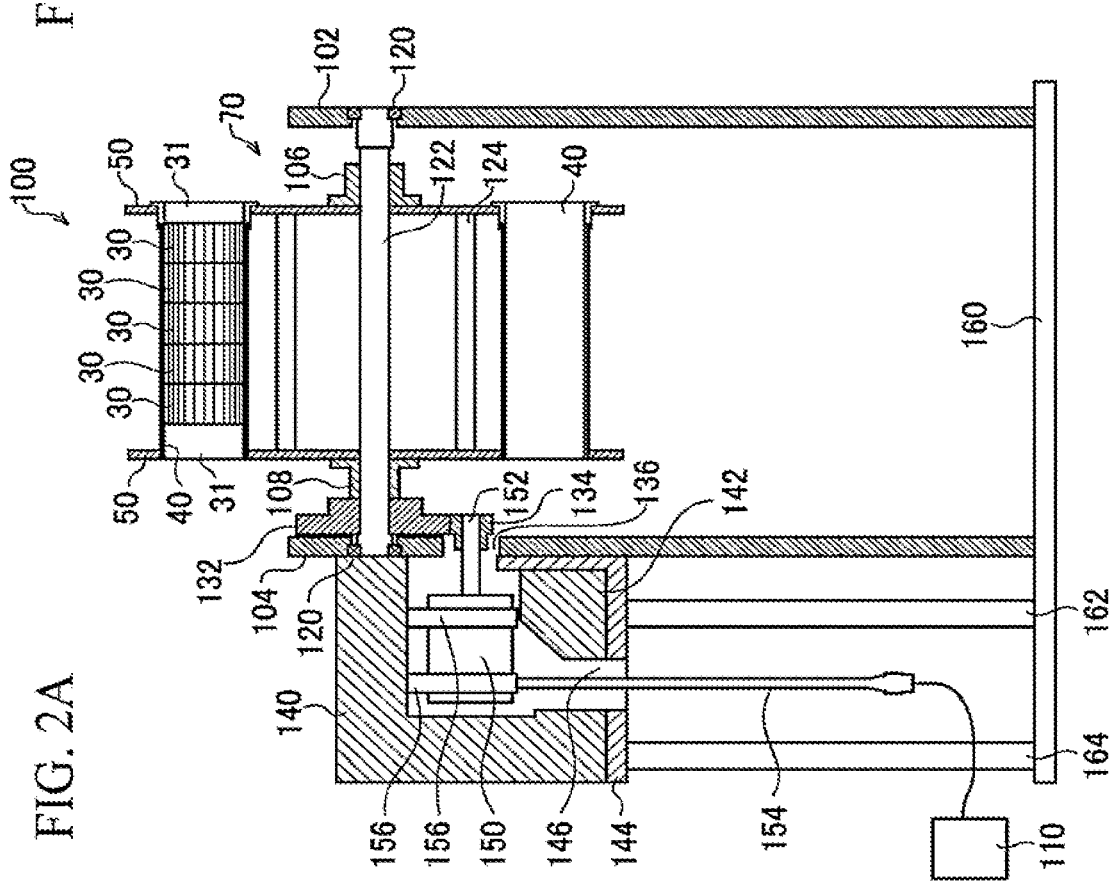

One embodiment of the neutron ray irradiation target apparatus 100 used for the above-described neutron ray irradiation will be described with reference to FIGS. 2A to 5. FIGS. 2A and 2B show views of the neutron ray irradiation target apparatus 100 according to the present invention, wherein FIG. 2B is its front view, and FIG. 2A is its right side view. Notably, the right side view of FIG. 2A shows a state in which a positioning member 31, which also serves as a spacer for determining the position of a closed container 30 in the axial direction, is removed. Notably, in the present embodiment, the irradiation targets 20 are seeds of a plant. However, the irradiation target is not limited to seeds of a plant and may be at least one member selected from a group consisting of seeds of a plant, embryo, the entirety of a plant, a portion of a plant, yeasts, and microorganisms.

The neutron ray irradiation target apparatus 100 includes a holding means 70 for fixedly holding the irradiation targets 20 at the time of neutron ray irradiation. The holding means 70 has a pair of plate-shaped members (circular plates) 50. A rotation shaft (center shaft) 122 is disposed in central portions of the plate-shaped members 50. The rotation shaft 122 is fitted into holes formed at the centers of the plate-shaped members 50. The pair of plate-shaped members 50 are connected to each other by the rotation shaft 122.

Each plate-shaped member 50 has a plurality of holes formed near an outer circumferential portion thereof at approximately equal intervals in the circumferential direction of the plate-shaped member 50. Stays 124 for keeping the distance between the pair of plate-shaped members 50 are fitted into the plurality of holes of the plate-shaped members 50.

Each plate-shaped member 50 has eight openings (slots) 42 formed in a radially inner portion thereof at approximately equal intervals in the circumferential direction (on its circumference). Tubular members 40 are selectively attached to the openings 42. Each tubular member 40 is fixedly supported, at its opposite ends in the axial direction, by the plate-shaped members 50, and is open at the opposite ends in the axial direction. One or more closed containers 30, whose structure will be described in detail later and which can accommodate the irradiation targets 20, can be attached to the tubular member 40. Notably, in the neutron ray irradiation target apparatus 100, the number of the slots 42 is 8. The number of the slots provided in the neutron ray irradiation target apparatus of the present invention is not limited to the above-described number. The neutron ray irradiation target apparatus is only required to have two or more slots. Although no particular limitation is imposed on the upper limit of the number of the slots, in general, the number of the slots is preferably 20 or less.

At least one closed container 30 can be attached to each slot 42. The closed container which is irradiated with the neutron ray can be changed simply by rotating the plate-shaped members 50 about the rotation shaft 122.

In FIGS. 2A and 2B, a position Pos1 corresponds to a position where the irradiation targets are irradiated with the neutron ray (hereinafter referred to as the "irradiation position"). Also, a position Pos2 is a position (hereinafter referred to also as a "standby position") which differs from the above-mentioned irradiation position. At each position, the closed container 30 is held on the circumference, and the closed container 30 located at the irradiation position can be changed by rotating the plate-shaped members 50 about the center shaft 122. The above-described operation is performed by controlling the rotational drive means by a control means. Therefore, an operator is not required to perform direct manual operation for changing the closed container 30 at the irradiation position. In general, at the time of neutron ray irradiation, the operator cannot enter a predetermined zone. However, in the present neutron ray irradiation target apparatus, the closed containers attached to the tubular members within the slots 42 beforehand can be sequentially moved to the neutron ray irradiation position by rotating the plate-shaped members 50.

Ball bearings 120 are attached to the opposite end portions of the rotation shaft 122, and the outer rings of the ball bearings 120 are held by rectangular support plates 102 and 104, respectively. The support plates 102 and 104 are perpendicularly fixed and attached to a base plate 160. Spacers 106 and 108 are attached to an intermediate portion of the rotation shaft 122 in the axial direction such that the spacers 106 and 108 are located on the outer side of the pair of plate-shaped members 50. The spacers 106 and 108 maintain a constant distance between the pair of plate-shaped members 50.

A large gear 132 is disposed between the support plate 104 and the spacer 108, which are located on one side. The large gear 132 is disposed to mesh with a small gear 134 fixedly attached to a motor shaft 152 of a motor 150. The support plate 104 has a hole 136 for gear movement which enables movement of the small gear 134 in the axial direction at the time of assembly.

The motor 150 is a horizontal shaft motor, and its circumferential portion is covered by shielding members 140 and 142 mounted on a mounting plate 144. As a result, damage of the motor 150 by neutron ray irradiation is prevented. Notably, the motor 150 is fixed to the shielding member 140 by a belt-shaped motor fixing member 156. A lead wire 154 for supplying electric power to the motor 150 is covered with a material which is resistant to neutron ray, and is led from an opening 146 formed between the shielding members 140 and 142 to a controller 110 disposed outside the vacuum environment.

A plurality of support pillars 162 and 164 are disposed below the mounting plate 144, and the height of the motor 150; i.e., the height at which the large gear 132 and the small gear 134 mesh with each other can be adjusted. When the controller 110 drives the motor 150, the holding means 70 is rotated, and the tubular member 40 located at the irradiation position Pos1 is replaced with the tubular member 40 located at the standby position Pos2.

It is preferred that components which constitute the above-described holding means 70, excluding the bearings, are formed of an aluminum material which is light and is less likely to be radioactivated, or a reduced-activation material which is one type of material composed of an element or an isotope component which reduce nucleus reactions by neutron, etc. A vanadium alloy, reduced-activation ferritic steel, a silicon carbide composite material composed of silicon carbide fibers and a matrix (ceramic composite material), oxide dispersion strengthened ferritic steel, which is one type of oxide dispersion strengthened alloy, a boron material, or the like is used as the reduced-activation material.

When the components are formed of the above-described materials, the half-life of radiation becomes shorter and safety is improved. Additionally, when the irradiation targets 20 or the neutron ray irradiation target apparatus 100 is carried out, the carrying out operation can be performed in an early stage. Notably, aluminum itself is less likely to be radioactivated. Meanwhile, since aluminum plates and aluminum rods are formed of an aluminum alloy material, they contain a small amount of manganese-55 (Mn-55), which is a stable nuclide. Therefore, when thermal neutron is applied to these materials, gamma-rays are released as a result of the capture reaction, whereby manganese-56 which is a radioactive isotope and whose half-life is 2.6 hours is generated. Accordingly, an effect that the irradiation targets 20 are irradiated secondarily with gamma-rays is also expected.

Figure 3A:
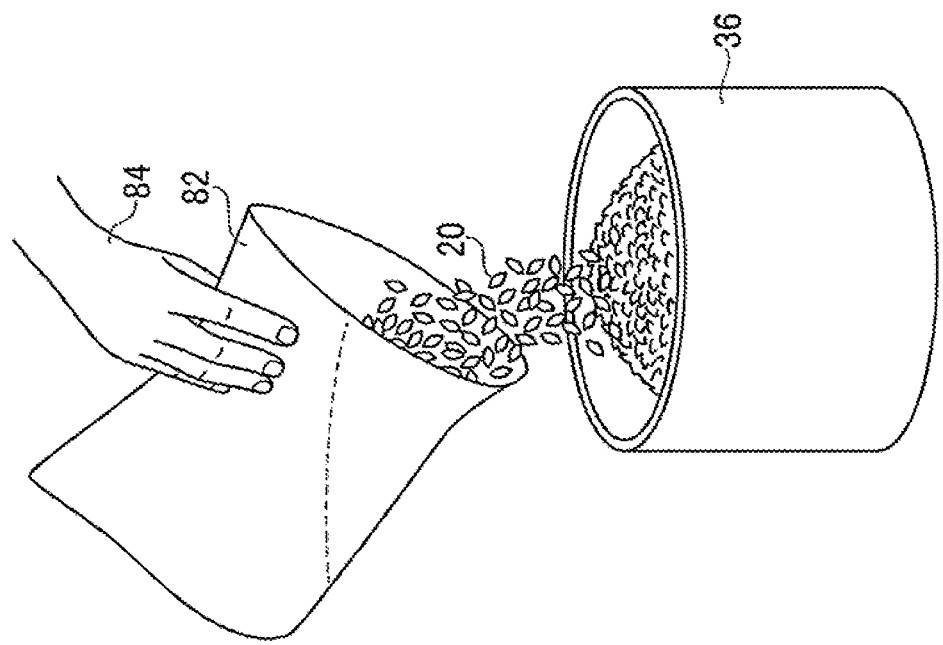
FIG. 3A is a schematic perspective view of a closed container of the neutron ray irradiation target apparatus shown in FIGS. 2A and 2B and a lid member of the closed container.
Figure 3B:
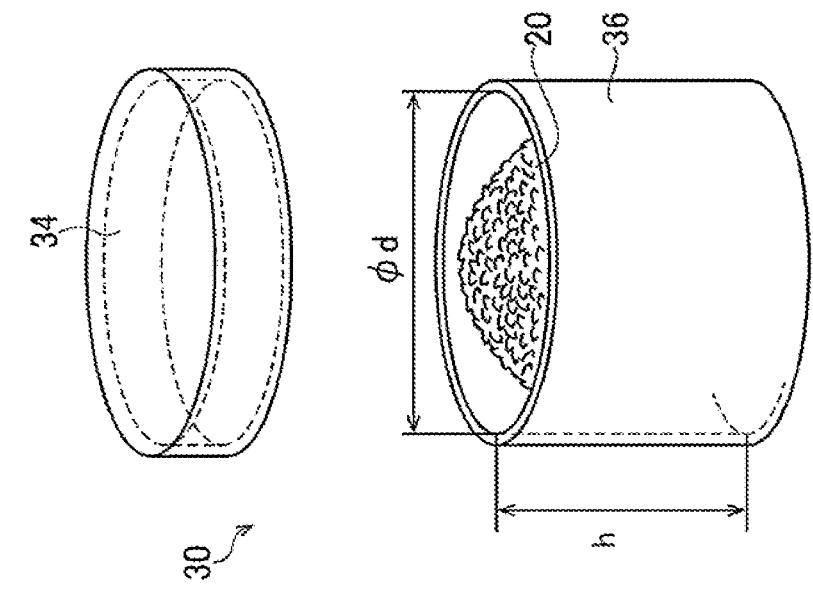
FIG. 3B is a view showing an operation of charging irradiation targets into the closed container.

FIGS. 3A and 3B show the details of the closed container 30 for accommodating the irradiation targets 20. FIG. 3A is an exploded perspective view of the closed container in a state in which the irradiation targets 20 are partially accommodated, and FIG. 3B is a view showing an example of a procedure for stacking the irradiation targets 20 in the closed container 30 "densely" or "three-dimensionally and randomly."

The closed container 30 is composed of a lower container 36 which is a portion for accommodating the irradiation targets 20, and an upper lid 34 which is fitted to the lower container 36. The outer and inner diameters of the upper lid 34 and the lower container 36 are set such that, when the upper lid 34 is fitted to the lower container 36, a gap is not formed substantially between the upper lid 34 and the lower container 36, or the gap formed between the upper lid 34 and the lower container 36 is small enough so that the accommodated irradiation targets 20 do not leak through the gap. Here, the depth of the lower container 36 is h, and the inner diameter of the lower container 36 is φd. Therefore, each closed container 30 can accommodate the irradiation targets 20 whose total volume is $\pi d^2 h/4$.

Notably, in the present embodiment, the closed container 30 is a metal can with a lid. However, a bag-shaped member with a zipper (plastic bag with a fastener), a plastic tube whose opposite end portions are sealed, or the like can be used as the closed container 30. In the case where the closed container 30 formed of the tube or the plastic bag with a fastener in which the irradiation targets 20 are accommodated in a sealed condition is directly accommodated in the tubular member 40, it is possible to obtain an action and effects similar to those obtained in the case where the above-described metal can-type closed container 30 is used.

The amount of the irradiation targets 20 which can be accommodated in the closed container 30 is measured in advance, and the measured amount of the irradiation targets 20 are placed in, for example, a bag 82. Subsequently, an operator holds the bag 82 with a hand 84 and inclines the bag 82, thereby pouring the irradiation targets 20 into the lower container 36 of the closed container 30. Finally, the operator levels the top surface with the hand 84, and then fits the upper lid 34 to the lower container 36. As a result of such a procedure, a portion of each irradiation target 20 is in contact with other irradiation targets 20 within the closed container 30. This state will be referred to as stacking "densely" or "three-dimensionally and randomly."

In other words, charging the irradiation targets 20 irregularly (in disorder) into the closed container 30 such that they come into contact with each other means stacking "densely" or "three-dimensionally and randomly" and is a concept which also encompasses pressing the irradiation targets 20 so as to increase the degree of closeness or contact among the irradiation targets 20 in a range in which the irradiation targets 20 are not physically damaged.

When the irradiation targets 20 are stacked in the closed container 30 "densely" or "three-dimensionally and randomly" as described above, as shown in FIGS. 4A to 4C, which will be described later, secondary radiation rays are generated in an irradiation target 20 irradiated with the neutron ray (this irradiation target will be denoted by, for example, 20*a*). This secondary radiation rays enter an irradiation target 20 (this irradiation target will be denoted by, for example, 20*b*) which is in contact with the irradiation target 20*a* irradiated with the neutron ray, and mutation may be induced in that irradiation target 20*b* as well. This action is repeated, and mutation may be induced in all the irradiation targets 20 charged in the closed container 30 "densely" or "three-dimensionally and randomly."

Specifically, the neutron ray is applied to an irradiation target (typically, $10^6$ to $10^7$ neutrons per $cm^2$ and per sec are applied at the irradiation position), neutrons collide with the irradiation target and a nucleus reaction occurs. The types of this nucleus reaction include "scattering" in which neutrons are bounced back after having collided with a target nucleus and "absorption" in which neutrons are taken into the target nucleus.

There are two types of scattering; i.e., elastic scattering and inelastic scattering. Each of these types of scattering may occur. Elastic scattering means scattering in which the internal state of the target nucleus does not change during the scattering process and in which neutrons are bounced off. In this case, a portion of the energy of each incident neutron becomes the kinetic energy of the atomic nucleus, and the kinetic energy of the neutron is partially lost.

Meanwhile, inelastic scattering means scattering in which a portion of the energy of each incident neutron is given to the target nucleus and its internal state changes. At that time, the energy given to the atomic nucleus is released in the form of gamma-rays.

"Absorption" means a reaction in which the neutron having collided with the target nucleus is captured by the target nucleus and does not come out from the target nucleus. At that time, protons, alpha particles, etc. come out; however, no neutron comes out. Therefore, this scattering is categorized as "absorption reaction." A reaction in which each incident neutron merely enters the target nucleus and other particles do not come out is called "capture," and the energy of the captured neutron is released in the form of gamma-rays. Accordingly, in the "capture" reaction, the neutron is lost.

Therefore, in the case where a neutron reacts with the atomic nucleus of the irradiation target at a certain probability, scattering of the neutron itself and release of secondary particle rays (alpha, proton, gamma) occurs mixedly. In some cases, the secondary particle rays are applied to a neighboring seed and damages its DNA. In some cases, scattered neutrons react with the nucleus of a seed adjacent thereto. In some cases, a scattered neutron collides with the atomic nucleus of an arbitrary seed in the direction in which the neutron is scattered, whereby the neutron is scattered again, or secondary particle rays are released. These reactions are repeated until the energy of the incident neutron first applied dissipates and a thermal equilibrium state is created.

In the above-described manner, neutron rays and secondary particle rays are successively applied to the irradiation targets accommodated in the closed container, so that mutation is induced in these irradiation targets successively.

Figure 4A:
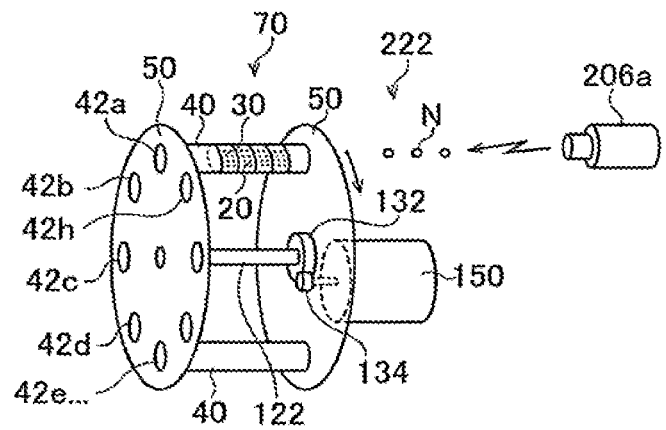
FIGS. 4A to 4C are illustrations used for describing the principle of neutron ray irradiation.
Figure 4B:
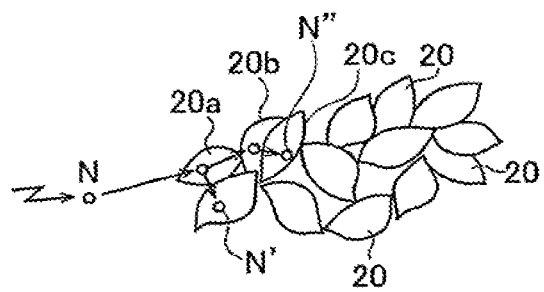
Figure 4C:
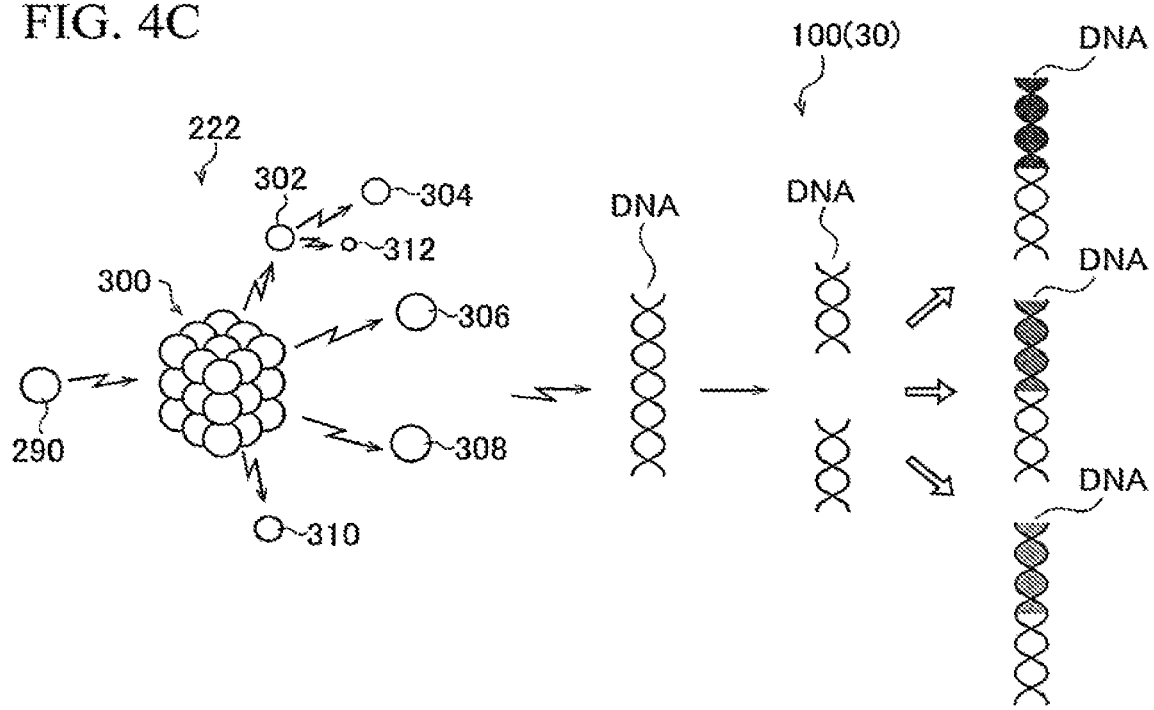

FIGS. 4A to 4C show the principle of induction of mutation. FIG. 4A is a model in which a neutron ray is applied to the irradiation targets 20 held in the holding means 70 of the neutron ray irradiation target apparatus 100 according to the present invention. FIG. 4B is a schematic illustration used for describing the effect of neutron ray irradiation between irradiation targets 20 contained in a container and located adjacent to each other. FIG. 4C is a further-microscopic illustration used for describing a quantum beam breeding model according to the present invention.

In the tubular member 40 attached to one slot 42a among the plurality of (eight in the present embodiment) slots 42a to 42h formed in the holding means 70, a plurality of (up to five in the present embodiment) closed containers 30 are stacked in the axial direction of the tubular member 40. In each closed container 30, plant seeds, which are the irradiation targets 20, are stacked "densely" or "three-dimensionally and randomly" and fill the closed container 30. Charged particles generated by a charged particle generation apparatus 206a provided in the accelerator and accelerated by the accelerator are applied to a target 222, whereby neutrons N are generated. The holding means 70 is rotated by the motor 150 via a speed reduction means composed of the large gear 132 and the small gear 134 such that the tubular member 40 is positioned at the position where the irradiation targets 20 are irradiated with the neutrons N. As a result, it becomes possible to apply the neutron to the irradiation targets 20 within the closed container 30.

In the closed container 30 of the neutron ray irradiation target apparatus 100 configured as described above, microscopically, the phenomenon shown in FIG. 4B occurs. Namely, in an irradiation target 20a directly irradiated with a neutron N generated at the target 222 as a result of irradiation with the charged particles, as a result of irradiation with the neutron N, nucleus reactions (scattering and absorption) occur, and secondary radiation rays (alpha-ray, proton-ray, gamma-ray) are generated. Thus, DNAs are cut by ionization. Also, the secondary radiation rays and the neutron N' (N prime) having undergone the nucleus reactions enter another irradiation target 20b which is located adjacent to the irradiation target 20a and is in contact with the irradiation target 20a. In some cases, in the irradiation target 20b, actions by the secondary radiation rays occur, and secondary radiation rays may be further generated as a result of entry of the neutron N'. The secondary radiation rays and the neutron N"(N double prime) enter still another irradiation target 20c which is located adjacent to the irradiation target 20b and is in contact with the irradiation target 20b.

Even when the secondary radiation rays are applied to the adjacent seed, the neutron ray does not always cause a nucleus reaction with the adjacent seed. The neutron ray may pass through the adjacent seed or may skip the adjacent seed and hit against another seed located adjacent to the adjacent seed. This phenomenon occurs stochastically. Namely, the applied neutron causes nucleus reactions with arbitrary seeds in many places and secondary radiation rays are generated, whereby the DNA chains of that seed and seeds located adjacent thereto are cut or damaged. Since the neutron ray is high in penetrability, the neutron ray hits against the atomic nucleuses of the constituent elements of an arbitrary seed stochastically. In this manner, reactions progress successively. In the present specification, this will be referred to also as the "skip-like domino toppling phenomenon (hereinafter referred to as the domino toppling for short).

Secondary radiation rays and neutrons are generated in succession like domino toppling. In other words, secondary radiation rays and (scattering) neutrons are applied to different irradiation targets one after another. As a result, secondary radiation rays and neutrons enter another irradiation target 20 which is located adjacent to and in contact with the first irradiation target 20. Alternatively, because of the penetrability of neutrons, neutrons enter another irradiation target 20 which is remote from the first irradiation target 20. As a result, DNA chains of the irradiation targets 20 are successively cut or damaged, whereby the probability of induction of mutation is increased. Notably, depending on the degree of nucleus reaction, the neutron ray N disappears at a certain stage due to dissipation of energy or passes through the group of seeds as it is.

FIG. 4C shows this state further schematically. In a target atomic nucleus 300 to which a charged particle beam P is applied, a large number of atoms are arranged regularly. When a proton 290 accelerated to 3 GeV by an accelerator is applied to the array of atoms, for example, a mercury target, the target atomic nucleus 300 therein generates a plurality of types of secondary particles and radiates them. The secondary particles include a pion 302, a neutron 306, an antiproton 308, and a kaon 310. Simultaneously, a muon 304 and a neutrino 312 are also generated. Among them, the neutron 306 is high in substance penetrability and exists over a long distance. Therefore, the neutron 306 is suitable for application to the irradiation target. The generated pulse neutron beam (the neutron 306) may have an intensity of up to 1 MW.

When the neutron 306 is applied to a seed of a plant, which is an irradiation target 20, a DNA of the plant is damaged at a high probability (i.e., is not always damaged). For example, the double strand of the DNA is cut. Then, cut DNAs are connected together in an arrangement different from the original DNA arrangement. As a result, for example, mutation is induced in a plant which originally has white flowers, whereby the plant is mutated to have, for example, large pink flowers, small pink flowers, or large white flowers.

FIG. 5 shows a change in the intensity of applied neutrons emitted from a neutron irradiation apparatus whose highest beam power is 1 MW, while changing the beam power.

The position where the intensity (energy) of the applied neutrons is measured is the sample position denoted by 42a in FIGS. 4A to 4C. It is possible to apply the neutron ray to the irradiation target 20 in various doses by changing the beam power and the irradiation time. Also, use of a thermal neutron blocker and a filter makes it possible to apply only desired fast neutrons to the irradiation targets 20 without applying high-energy neutrons, which is a mixture of various types of neutrons such as thermal neutrons and fast neutrons. Thus, the mutation induction ratio can be increased efficiently by controlling the type of neutrons and irradiation dose.

EXAMPLES

Figure 7A:
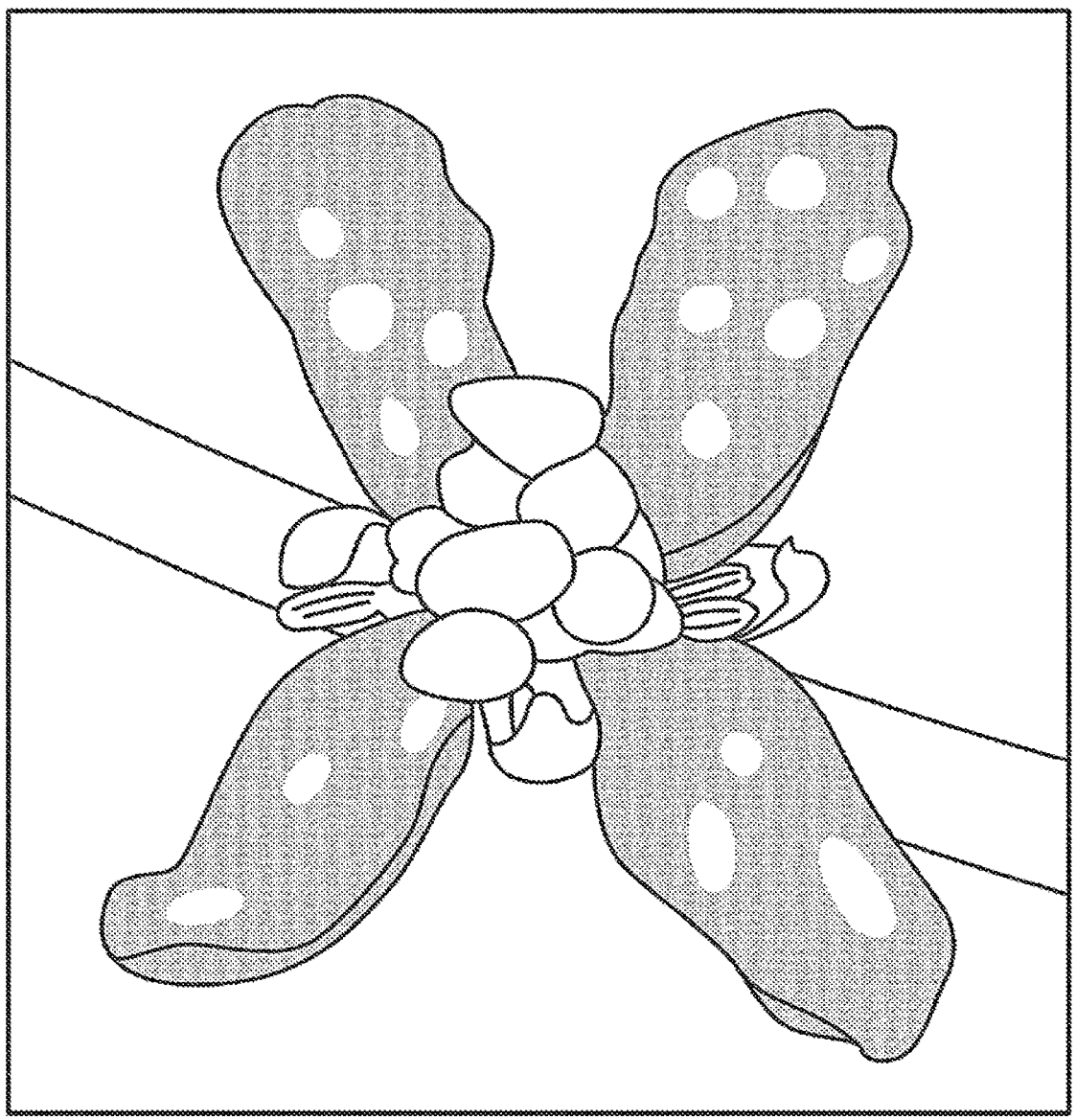
FIG. 7A is a sketch showing an induced mutation (petal mutation and pistil anomaly).
Figure 7B:
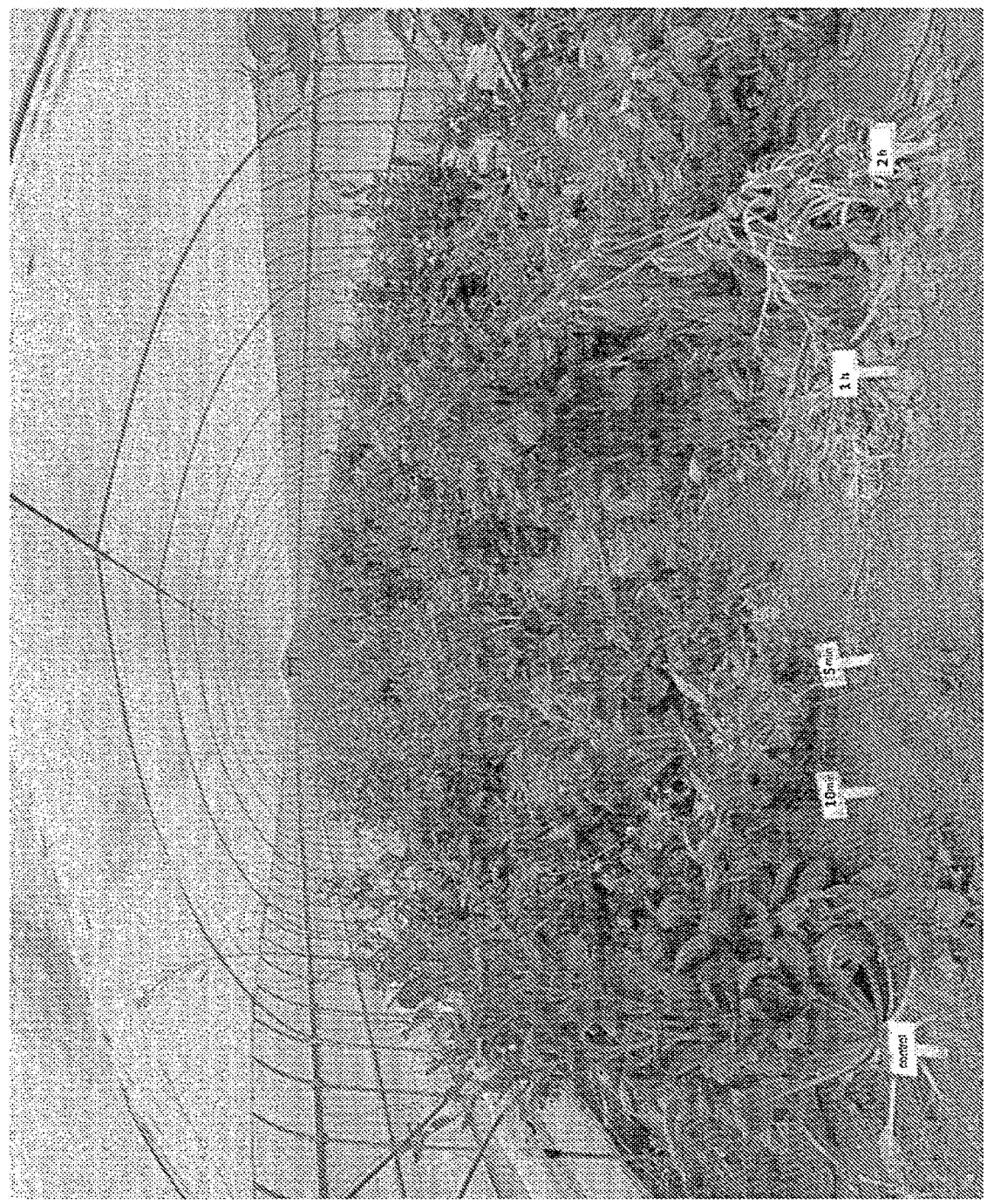
FIG. 7B is a photograph showing an induced mutation (dwarf).
Figure 7C:
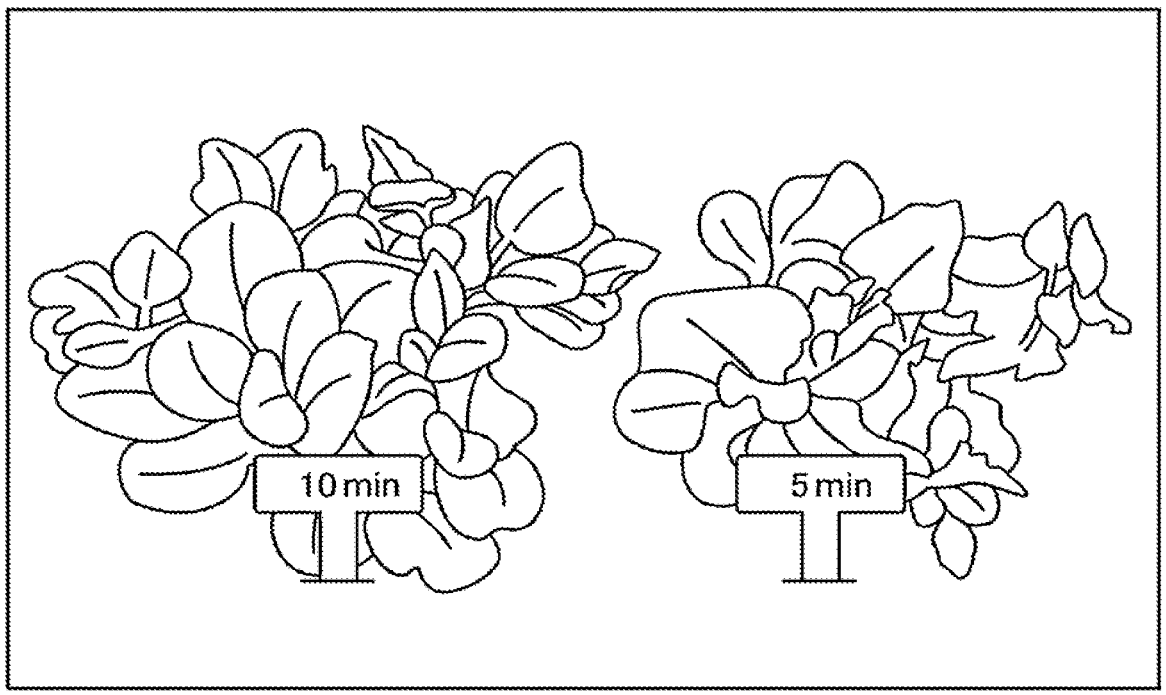
FIG. 7C is a sketch showing an induced mutation (dwarf).

FIGS. 6 and 7A to 7C show examples of the results of tests performed by using the above-described accelerator of J-PARC. FIG. 6 is a table which shows changes in the number and ratio (%) of occurrences of biological mutation, which changes occurred when the irradiation time of a neutron ray applied to a certain number of seeds of komatsuna was changed. FIGS. 7A to 7C include sketches and a photograph which show an example of the test results. Seeds of komatsuna are divided into groups each containing about 250 seeds, and the irradiation time was changed to 5 minutes, to 10 minutes, to 1 hour, and to 2 hours. CTRL (control) refers to a control group of seeds to which the neutron ray was not applied (the irradiation time: 0 minute). Main types of mutation include pistil anomaly, bolting anomaly, and petal mutation. Occurrence of the above-described mutations will be described briefly below with reference to the sketches and photograph shown in FIGS. 7A to 7C.

The petal mutation appears on yellow petals of komatsuna in the form of white spots. In FIG. 7A, spots appear on each of four petals at a plurality of locations such that the area of the spots accounts for one severalth of the entire area thereof. The pistil anomaly refers to generation of a plurality of pistils in a flower in which only one pistil is generated normally. In FIG. 7A, a pistil protrudes from a pistil, which shows that a gene signaling the end of growth was knocked out. Although this mutation does not so much influence the growth of komatsuna, this is an anomaly that can be clearly distinguished morphologically.

FIG. 7B is a photograph showing dwarf which greatly influences the growth of komatsuna, and FIG. 7C is a sketch of a portion thereof. These sketch and photograph show the process of growth of komatsuna which was rendered dwarf by irradiation with neutron rays. A komatsuna plant which has grown normally (CTRL, a Komatsuna plant in front of which a plate saying "control" stands in FIG. 7B) has a plant height of about 1.6 m. In contrast, komatsuna plants having undergone the neutron ray irradiation (of komatsuna plants shown in FIG. 7B, those in front of which plates saying "5 minutes," "10 minutes," "1 hour," and "2 hours," respectively stand, and a komatsuna plant shown by the sketch of FIG. 7C) have small plant heights of about several tens of centimeters. The komatsuna plants which were rendered dwarf have low heights, and their leaves have deep colors and are stiff and wavy.

As a matter of course, in the case of seeds not having undergone the neutron ray irradiation, the mutation generation ratio (excluding natural generation ratio) is 0%. In contrast, mutation generation ratios obtained by changing the irradiation time are as follows. In the case of petal mutation (an orange-color spot pattern on a white background), the obtained mutation generation ratios were 0% (CTRL), 10% (the irradiation time: 5 minutes), 6% (10 minutes), 18% (1 hour), and 36% (2 hours), respectively. However, in the case where the neutron ray was applied for two hours, since the irradiation time was relatively long and the irradiation dose was higher, in 36% of all the komatsuna plants, no petal was formed and morphological anomalies, such as failure of seeding, appeared, whereby pistil anomaly occurred. Notably, unlike soft cells of roots or cotyledons already formed in the state of seed, petals or bolting is produced as a result of cell division. Therefore, their biological mutations or anomalies occurred as a result of damage to DNAs by the neutron ray.

In the case of pistil anomaly (mutation), the obtained mutation generation ratios were 5% (CTRL), 16% (the irradiation time: 5 minutes), 6% (10 minutes), 19% (1 hour), and 36% (2 hours), respectively. However, in the case where the neutron ray was applied for two hours, since the irradiation dose was high, in 36% of all the komatsuna plants, no petal were formed, and a pistil anomaly of failing to seed occurred. Such a pistil anomaly occurred at a ratio of 5% also in the case of CTRL. However, when the case of 10-minute irradiation is excluded, statistically significant differences exist.

In the case of bolting anomaly (mutation), the obtained mutation generation ratios were 5% (CTRL), 10% (the irradiation time: 5 minutes), 6% (10 minutes), 4% (1 hour), and 17% (2 hours), respectively. In the case where the neutron ray was applied for two hours, 17% of all the komatsuna plants failed to bolt, which means that the exposed amount of the neutron ray was such that the komatsuna plants were not able to have flowers and seeds. Even in the case of CTRL or the case where the neutron ray was applied for 10 minutes or 1 hour, about 5% of all the komatsuna plants failed to bolt. However, this ordinally occurs even in the natural world. These results show that a statistically significant difference exists when the neutron ray irradiation time is 5 minutes or 2 hours.

Namely, the ratio of mutation generation due to neutron ray irradiation is 6 to 36% when the irradiation time is in the range of 5 minutes to 2 hours, and the probability of obtainment of useful mutations is several percentages, which is about 10% of all the mutations. That is, the probability of obtainment of useful mutations is on the order of 0.1 to 1%. The mutation induction ratios are extremely higher than those in the case of other radioactive rays; i.e., X-ray or gamma-ray (0.01%), heavy ion beam (0.01 to 0.1%) and those under the natural environment in which no artificial radioactive ray is applied (0.0001 to 0.001%). This reveals that neutron irradiation is extremely effective in inducing mutations.

Meanwhile, as to the absolute number of seeds in which mutations have been induced, the following was found. The case where a heavy ion beam which is the highest in irradiation effect among radioactive rays, excluding neutron ray, is considered, as a comparative example, by using the case of heavy particle beam irradiation described in Patent Document 4 as an example. Although the heavy ion beam is a high LET ray like the neutron ray, its substance penetrability is low (several tens of micrometers from the surface of a substance), and therefore, the heavy ion beam can treat only irradiation targets in a surface layer disposed on an irradiation surface.

Namely, it is necessary to dispose seeds (irradiation targets) in a surface layer such that the irradiation targets are a predetermined distance (100 mm in the case of ions of carbon C) away from an irradiation window and their embryos face upward. Also, it is necessary to perform depth control. As a result, the number of seeds which can be simultaneously irradiated is about 150, which is the number of seeds in one layer of cells (containers or the like). Since 30 cells (3 cells×10 stacks) can be irradiated with a heavy ion beam by using an irradiation target apparatus, only 150 (seeds)×30=4500 (seeds) can be irradiated with the heavy ion beam at a time.

Meanwhile, in the case of the neutron ray irradiation target apparatus 100 according to the present invention, which was used for neutron ray irradiation, about 6,000 (in the case of seeds of komatsuna) seeds (irradiation targets 20) can be charged into each closed container 30, and five closed containers 30 can be held in each tubular member 40. Also, since the holding means 7 has eight slots, eight tubular members 40 can be held. Thus, the neutron ray irradiation target apparatus 100 enables 6,000×5×8=240,000 irradiation targets 20 to be irradiated with neutrons in a single test.

In the case of irradiation with the heavy ion beam, as described above, about 4,500 seeds can be irradiated with the heavy ion beam at a time by using an apparatus having approximately the same size as the apparatus used in the present test. In contrast, when the neutron ray irradiation target apparatus 100 of the present invention is used, as described above, about 240,000 seeds can be irradiated with the neutron ray. Namely, the ratio—in number of seeds which can be irradiated with a particle beam in a single test—between the case of heavy ion beam and the case of neutron ray is about 4,500:240,000≈1:53.3. By using a neutron ray as an irradiation source, it becomes possible to irradiate a large amount of seeds with a particle beam. In addition, since the ratio of induction of mutations through irradiation with the neutron ray is higher than that in the case of irradiation with the heavy ion beam, the number of mutated seeds obtained through a single-time irradiation is considerably larger than that in the case where the heavy ion beam is used.

Namely, the mutation induction ratio of the heavy ion beam is 0.01 to 0.1%, and the number of irradiation targets (seeds) irradiated with the heavy ion beam at a time is about 4,500. In contrast, the mutation induction ratio of the neutron ray is 0.1 to 1%, and the number of irradiation targets (seeds) irradiated with the neutron ray at a time is about 240,000. Therefore, whereas the number of induced mutations is less than 5 in the case of the heavy ion beam, the number of induced mutations is about 240 to about 2,400 in the case of the neutron ray. When the neutron ray is used, a larger number of mutated seeds can be obtained as compared with other methods, and the probability of obtaining a desired useful species can be increased considerably. As a result, it was confirmed that places, human resources, and periods which are needed for breeding can be reduced.

FIGS. 8A and 8B show another example of the neutron ray irradiation target apparatus according to the present invention by a front view (FIG. 8A) and a right side view (FIG. 8B) as in the case of FIGS. 2A and 2B. The present neutron ray irradiation target apparatus 100b has a holding means which differs from that of the neutron ray irradiation target apparatus 100 shown in FIGS. 2A and 2B. In the holding means 70b, a through hole is formed at the center of a circular columnar rotating body 60, and the rotation shaft 122 is inserted into that through hole. The rotating body 60 has a plurality of (8 in the present embodiment) blind holes 44 which are formed at a position located radially inward from the outer circumference of the rotating body 60 such that the blind holes 44 are located at approximately equal intervals in the circumferential direction. The opening side of each blind hole 44 is the side where the neutron ray N is applied.

A tubular member 40 similar to that shown in FIGS. 2A and 2B is attached to at least one of the blind holes 44. A closed container 30 held in the tubular member 40 is the same as that shown in FIGS. 2A and 2B, and irradiation targets 20 are similarly charged "densely" or "three-dimensionally and randomly." The tubular member 40 is formed of an aluminum alloy for weight reduction. However, in the case where further weight reduction is needed, the material around the blind hole portions is removed for weight reduction. In the case of the present embodiment, effects similar to those attained in the case of FIGS. 2A and 2B are obtained, and the number of components is smaller.

Figure 9:
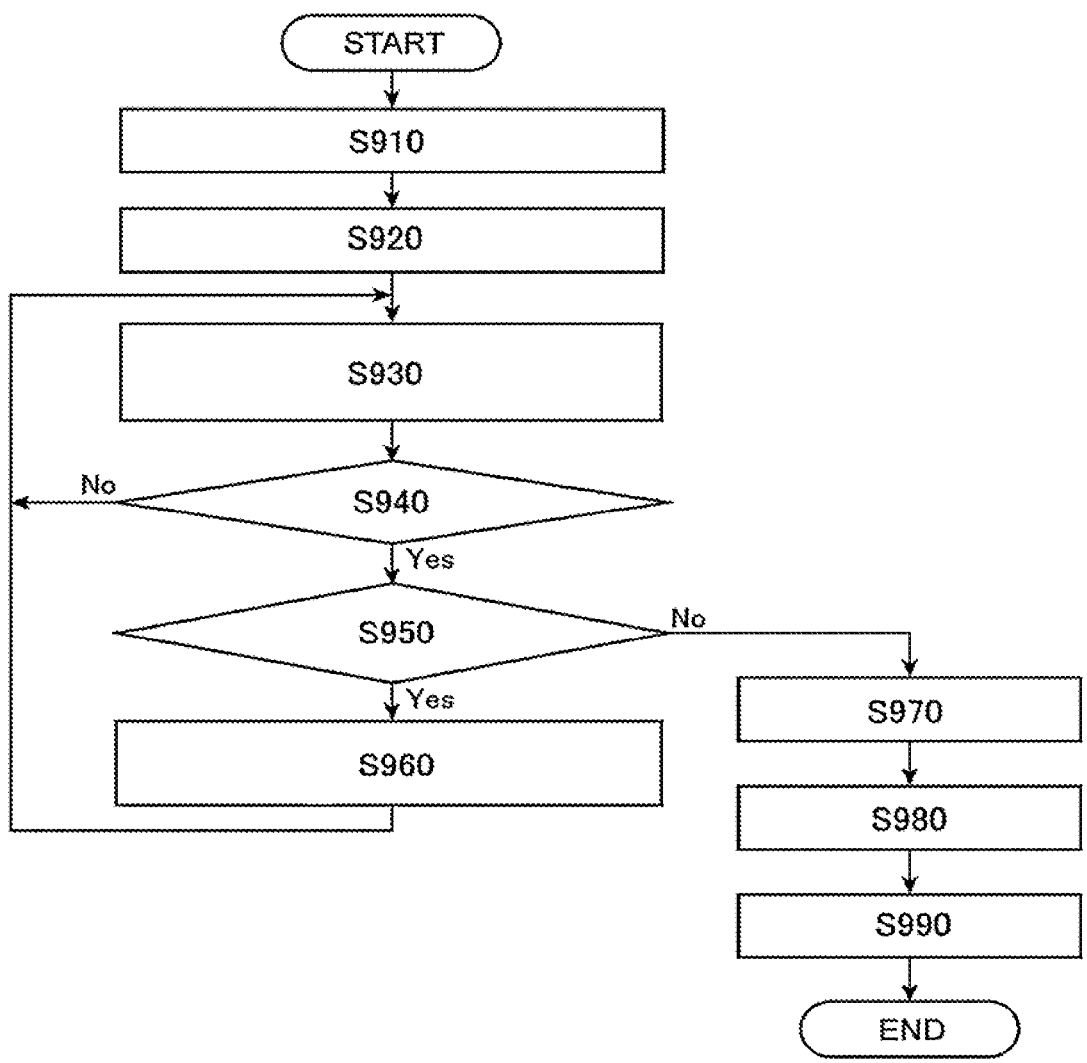
FIG. 9 is a flowchart showing a method for inducting mutation by neutron ray irradiation.

FIG. 9 shows a flowchart of a method for inducing mutations by applying a neutron ray to the irradiation targets 20 by using the neutron ray irradiation target apparatus 100 described in either of the above-described embodiments. First, the volume or weight of seeds of a plant (irradiation targets) 20 is measured. Subsequently, a predetermined amount of seeds are stacked and charged in each closed container 30 "densely" or "three-dimensionally and randomly" (step S910). In the present embodiment, about 6,000 seeds whose volume or weight has been measured are charged in each closed container 30 formed of an aluminum alloy. Here, the irradiation targets (seeds) 20 are densely charged in each closed container 30 so that most irradiation targets 20 are in contact with each other. The irradiation targets 20 are, for example, seeds of a plant, their embryos, or the entirety or part of a plant. In the case where the entirety or part of a plant is charged, any of an aluminum alloy container, a glass container, or a plastic container, which have been sterilized, is used as a closed container 30.

A desired number of closed containers 30 filled with the irradiation targets 20 are prepared and held in the tubular member(s) 40 (step S920). In the neutron ray irradiation target apparatus 100 shown in the above-described embodiment, each tubular member 40 can accommodate up to 5 containers. Therefore, when the number of the closed containers 30 is 6 or more, a plurality of tubular members 40 are used. Notably, in the case where the holding means 70 shown in FIGS. 2A and 2B is used, it is preferred that an even number of tubular members 40 be disposed rotational symmetrically about the rotation shaft for the purpose of balancing.

In step S930, the neutron ray N having a predetermined intensity is applied to the tubular member 40 located at the irradiation position. The applied neutron ray contains cold neutrons ($E<0.026$ eV), thermal neutrons ($0.001<E<0.01$ eV), epithermal neutrons ($0.1<E<100$ eV), slow neutrons ($0.1<E<1000$ eV), intermediate neutrons ($1<E<500$ keV) or fast neutrons ($0.5<E<20$ MeV). Alternatively, the neutron ray is a mixture of these neutrons. The dose of the neutron ray is controlled by adjusting the energy of the neutron ray and the irradiation target irradiation time and is set to a range of 0.01 to 110 Gy.

In the case where the tubular member 40 is not located at the irradiation position, the tubular member 40 holding the closed containers 30 is moved to the irradiation position by driving the motor 150. When the irradiation targets (seeds or the like) 20 charged densely into the closed containers 30 are irradiated with the neutron ray, since the neutron ray is a high LET ray which is high in biological effect, secondary particle rays (alpha-ray, proton-ray, gamma-ray) are generated in a substance such as seeds due to high substance penetrability of the neutron ray and nucleus reactions. The secondary particle rays cut DNAs. As a result of irradiation of the irradiation targets 20 with the neutron ray, DNAs are damaged. Thus, a high irradiation effect and a high mutation induction ratio are realized.

In step S940, an unillustrated controller determines whether or not the irradiation time has elapsed. The irradiation time is set, as an "irradiation pattern," beforehand in accordance with the type and/or amount of irradiation targets. For example, the irradiation time is set to 5 min, 10 min, 1 Hr, 2 Hr, etc. When the predetermined time has not yet elapsed, the irradiation is continued. When the predetermined time has elapsed, the process proceeds to step S950.

In step S950, the unillustrated controller determines whether or not there still exist irradiation targets 20 not irradiated with the neutron ray N (hereinafter referred to as "unirradiated targets 20"). In the case where the unirradiated targets 20 still remain, the process proceeds to step S960. In step S960, the tubular member 40 holding the unirradiated targets 20 is moved to the irradiation position by the motor 150. Subsequently, the process returns to step S930.

Namely, in accordance with a predetermined irradiation pattern (typically, irradiation time), a certain group of irradiation targets is irradiated with the neutron ray. After that, the rotational drive means operates so that a different group of irradiation targets are moved to the irradiation position, and the different group of irradiation targets are irradiated with the neutron ray in accordance with the predetermined irradiation pattern. During this process, the rotational drive means operates intermittently.

In step S950, if all the irradiation targets 20 have been irradiated, the entire neutron ray irradiation target apparatus 100 containing the radioactivated irradiation targets 20 is cooled (step S970). The radioactivated irradiation targets 20 are cooled until a period equal to or shorter than the half decay period of the radioactivated irradiation targets 20 has passed, and the radiation dose becomes lower than the standard radiation dose of the facility in which the neutron ray irradiation apparatus 10 is installed, and the irradiation targets can be removed.

When the radiation dose level decreases to the standard radiation dose or less, the neutron ray irradiation target apparatus 100 is taken out from the neutron ray irradiation apparatus 10, and the closed containers 30 are removed from the neutron ray irradiation target apparatus 100 (step S980). Furthermore, the upper lids 34 of the closed containers 30 are opened, and the irradiation targets 20 are taken out therefrom.

In step S990, the taken out irradiation targets 20 are checked to determine whether or not mutations have been induced therein. Notably, the determination as to whether or not mutations have been induced can be made by conventionally used various methods; for example, DNA marker, genome analysis, cultivation of neutron-irradiated seeds, cultivation of seeds of their children's generation, or the like.

As described above, in the embodiments of the present invention, irradiation targets are irradiated with a neutron ray. Therefore, not only irradiation targets facing an irradiation surface but also irradiation targets which do not directly face the irradiation surface (i.e., are not exposed) are irradiated with LET rays by a domino toppling effect. As a result, a large number of irradiation targets can be irradiated with the neutron ray through a single-time neutron irradiation, whereby the mutation induction ratio can be increased remarkably. Even when the surface irradiated with neutrons is limited, since the position of each tubular member which holds irradiation targets can be changed by rotation of the holding means, the neutron ray can be applied to a plurality of tubular members substantially continuously, and the irradiation targets held in each tubular member can be irradiated with the neutron ray without fail.

Also, in the case where mutations are generated by using neutrons, since the neutron ray has substance penetrability, it is possible to delete certain areas of the base sequences of DNAs together by nucleus reactions within seeds without damaging the seeds so much. Therefore, it is possible to easily induce mutations while suppressing generation of physiological anomalies such as failure to bud. In the above-described embodiments, advantages of such neutron ray irradiation can be utilized maximally.

DESCRIPTION OF REFERENCE NUMERALS

7: holding means, 10: neutron ray irradiation apparatus, 20: irradiation target, 31: positioning member, 34: upper lid, 36: lower container, 40: tubular member, 42: opening, 42a: slot, 44: blind hole, 50: plate-shaped member, 55: stable nuclide manganese, 56: radioactive isotope manganese, 60: rotating body, 70: holding means, 82: bag, 84: hand, 100, 402, 404, 406, 408: neutron ray irradiation target apparatus, 102, 104: support plate, 106, 108: spacer, 110: control apparatus, 120: ball bearing, 122: rotation shaft, 124: stay, 132: large gear, 134: small gear, 136: hole, 140, 142: shielding member, 144: mounting plate, 146: opening, 150: motor, 152: motor shaft, 154: lead wire, 156: motor fixing member, 160: base plate, 162, 164: support pillar, 200: accelerator, 202, 204, 212, 213, 218: pipe passage, 206: linac, 206a: charged particle generation apparatus, 208, 210: synchrotron, 220: life science experimental facility, 222: target, 226: collimator, 230: experiment building, 232: slit, 234: chopper, 236: filter, 238: collimator, 240: slit, 290: proton, 300: target atomic nucleus, 302: pion, 304: muon, 306: neutron, 308: antiproton, 310: kaon, 312: neutrino

The invention claimed is:

1. A neutron ray irradiation target apparatus which is used for irradiating irradiation targets with a neutron ray generated by a neutron ray irradiation apparatus, each of the irradiation targets being at least one member selected from a group consisting of a seed of a plant, an embryo of a plant, the entirety or part of a plant, yeast, and microorganisms, wherein the neutron ray irradiation target apparatus comprises holding means for holding the irradiation targets and is characterized in that
    the holding means holds at least one closed container which can accommodate the irradiation targets stacked randomly and three-dimensionally therein,
    the irradiation targets three-dimensionally stacked and accommodated in the at least one closed container is irradiated with the neutron ray which is adjusted to become a collimated beam,
    the neutron ray contains fast neutrons, and an irradiation dose of the fast neutrons is 110 Gy or less,
    a center shaft is disposed in a central portion of the holding means, and the neutron ray irradiation target apparatus comprises rotational drive means for rotatively driving the center shaft and control means for controlling the rotational drive means,
    the at least one closed container is held on the holding means at a plurality of positions, and the control means intermittently drives the rotational drive means in accordance with an irradiation pattern determined beforehand, thereby changing the at least one closed container which is to be irradiated with the neutron ray, and
    a thermal neutron blocker or a filter is used for applying only a high LET ray to the irradiation targets.

2. The neutron ray irradiation target apparatus according to claim 1, wherein the holding means comprises a plurality of tubular members each of which is opened at at least one end in an axial direction, and a pair of plate members which fixedly support opposite ends of the tubular members in the axial direction, wherein the at least one closed containers is fixedly held in at least any one of the plurality of tubular members.

3. The neutron ray irradiation target apparatus according to claim 2, wherein the holding means has a plurality of slots each of which is opened at at least one end in the axial direction, and the tubular members can be individually attached to the slots.

4. The neutron ray irradiation target apparatus according to claim 1, characterized in that each of the irradiation targets held in the at least one closed container is a seed or embryo of a plant.

5. The neutron ray irradiation target apparatus according to claim 1, characterized in that each of the irradiation targets held in the at least one closed container is the entirety or part of a plant.

6. The neutron ray irradiation target apparatus according to claim 4, characterized in that the neutron ray emitted from the neutron ray irradiation apparatus contains high energy neutrons.

7. A mutation induction method performed by using a neutron ray irradiation target apparatus in which irradiation targets, held in at least one closed container provided in the neutron ray irradiation target apparatus are irradiated with neutrons generated by a neutron ray irradiation apparatus, so as to damage DNAs of the irradiation targets, thereby inducing mutations, each of the irradiation targets being at least one member selected from a group consisting of a seed of a plant, an embryo of a plant, the entirety or part of a plant, yeast, and microorganisms, the mutation induction method being characterized by comprising the steps of:

holding in the neutron ray irradiation target apparatus by a holding means the at least one closed container which accommodates the irradiation targets stacked randomly and three-dimensionally, wherein the at least one closed container is held on the holding means at a plurality of positions;

irradiating the irradiation targets with a neutron ray which is adjusted to become a collimated beam from the neutron ray irradiation apparatus while rotating the holding means around a center shaft disposed in a central portion of the holding means and using a thermal neutron blocker or a filter for applying only a high LET ray to the irradiation targets, the neutron ray contains fast neutrons, wherein an irradiation dose of the fast neutrons is 110 Gy or less;

cooling the irradiation targets radioactivated as a result of irradiation with the neutron ray; and taking out the irradiation targets from the neutron ray irradiation target apparatus.

8. A method for manufacturing irradiation targets which are accommodated in at least one closed container and in which mutations have been induced, each of the irradiation targets being at least one which is selected from a group consisting of a seed of a plant, an embryo of a plant, the entirety or part of a plant, yeast, and microorganisms, the at least one closed container accommodating the mutated irradiation targets stacked randomly and three-dimensionally, the method being characterized by comprising inducing mutations in the irradiation targets by the mutation induction method as set forth in claim 7, thereby obtaining the mutated irradiation targets accommodated in the at least one closed container.

* * * * *